US010066566B2

(12) United States Patent
Knuebel et al.

(10) Patent No.: US 10,066,566 B2
(45) Date of Patent: Sep. 4, 2018

(54) METHOD AND DEVICE FOR OPERATING A PARTICLE SENSOR

(71) Applicant: Robert Bosch GmbH, Stuttgart (DE)

(72) Inventors: Andreas Knuebel, Stuttgart (DE); Enno Baars, Leonberg (DE); Michael Bessen, Stuttgart (DE)

(73) Assignee: Robert Bosch GmbH, Stuttgart (DE)

(*) Notice: Subject to any disclaimer, the term of this patent is extended or adjusted under 35 U.S.C. 154(b) by 210 days.

(21) Appl. No.: 15/038,134

(22) PCT Filed: Nov. 12, 2014

(86) PCT No.: PCT/EP2014/074368
§ 371 (c)(1),
(2) Date: May 20, 2016

(87) PCT Pub. No.: WO2015/074928
PCT Pub. Date: May 28, 2015

(65) Prior Publication Data
US 2016/0281623 A1    Sep. 29, 2016

(30) Foreign Application Priority Data

Nov. 20, 2013  (DE) .................. 10 2013 223 630

(51) Int. Cl.
*G01N 15/00*     (2006.01)
*F02D 41/14*     (2006.01)
(Continued)

(52) U.S. Cl.
CPC ......... *F02D 41/1494* (2013.01); *F01N 3/021* (2013.01); *F01N 11/00* (2013.01);
(Continued)

(58) Field of Classification Search
CPC ............ F02D 41/1466; F02D 41/1494; G01N 15/0606; G01N 15/0656; G01N 25/20;
(Continued)

(56) References Cited

U.S. PATENT DOCUMENTS

2010/0132680 A1    6/2010  Iwahashi
2011/0015824 A1*   1/2011  Ante ................... F02D 41/1466
                                              701/29.2
(Continued)

FOREIGN PATENT DOCUMENTS

CN    101688496 A    3/2010
DE    10133384      1/2003
(Continued)

OTHER PUBLICATIONS

International Search Report for Application No. PCT/EP2014/074368 dated Jan. 23, 2015 (English Translation, 2 pages).

*Primary Examiner* — Blake A Tankersley
(74) *Attorney, Agent, or Firm* — Michael Best & Friedrich LLP

(57) ABSTRACT

The invention relates to a method and to a device, in particular a control and evaluating unit, for operating a particle sensor (20) for determining a particle content in a gas flow, wherein the particle sensor (20) has, on the surface of the particle sensor, a sensor structure for determining a soot load and at least one heating element (26) separated from the sensor structure by an insulating layer, by means of which at least one heating element the particle sensor (20) can be heated up in a regeneration phase and in the process a soot load on the particle sensor (20) can be removed, and by means of the heating element (26) a heating phase can be performed at least at times before the regeneration phase, wherein in said heating phase a temperature that is significantly lower than the regeneration temperature is set, wherein short-term temperature drops as a result of wetting (Continued)

with water can be detected by means of a temperature sensor (27) integrated in the particle sensor (20). According to the invention, during the heating phase before the regeneration phase, the duration of the heating phase is extended if a temperature deviation from a certain temperature bandwidth around a temperature target value is detected for a certain time. Thus, it can be achieved that the sensor element is always completely dried throughout the sensor element, such that regeneration can be performed at high temperatures without damage as a result of thermal shock to the sensor element.

10 Claims, 1 Drawing Sheet

(51) Int. Cl.
  *G01N 15/06* (2006.01)
  *F01N 11/00* (2006.01)
  *F01N 3/021* (2006.01)
  *G01K 7/18* (2006.01)

(52) U.S. Cl.
  CPC .......... *F01N 11/002* (2013.01); *F01N 11/007* (2013.01); *F02D 41/1446* (2013.01); *F02D 41/1466* (2013.01); *G01N 15/0606* (2013.01); *G01N 15/0618* (2013.01); *G01N 15/0656* (2013.01); *F01N 2560/05* (2013.01); *F01N 2560/06* (2013.01); *F01N 2560/20* (2013.01); *G01K 7/18* (2013.01); *G01N 2015/0681* (2013.01); *Y02T 10/20* (2013.01); *Y02T 10/47* (2013.01)

(58) Field of Classification Search
  CPC .......... F01N 2560/05; F01N 2560/025; F01N 2560/20; F01N 2560/06
  See application file for complete search history.

(56) References Cited

U.S. PATENT DOCUMENTS

| | | | |
|---|---|---|---|
| 2011/0047978 A1 | 3/2011 | Zawacki et al. | |
| 2013/0283887 A1* | 10/2013 | Ante | F01N 9/002 73/28.01 |

FOREIGN PATENT DOCUMENTS

| | | | | |
|---|---|---|---|---|
| DE | 102007014761 | | 10/2008 | |
| DE | 102008040593 | * | 9/2009 | ............ F02D 41/14 |
| DE | 102008031648 | | 1/2010 | |
| DE | 102009003091 | | 11/2010 | |
| DE | 102009028319 | | 2/2011 | |
| DE | 102010002979 | * | 9/2011 | ............ G01N 25/20 |
| DE | 102012008462 | | 10/2012 | |

* cited by examiner

METHOD AND DEVICE FOR OPERATING A PARTICLE SENSOR

BACKGROUND OF THE INVENTION

The invention concerns a method for operating a particle sensor for determining a particle content in a gas flow, wherein the particle sensor comprises on the surface thereof a sensor structure for determining a soot load and at least one heating element that is separated from the sensor structure by an insulating layer and with which the particle sensor can be heated up in a regeneration phase, and in doing so a soot load on the particle sensor can be removed, and a heating phase can be carried out with the heating element at least at times before the regeneration phase, wherein a significantly lower temperature compared to the regeneration temperature is controlled in said heating phase, wherein brief drops in temperature as a result of wetting by water can be detected with a temperature sensor integrated within the particle sensor.

The invention further concerns a device, in particular a control and analysis unit, for operating the particle sensor and for performing the method according to the invention.

Particle sensors (PM) are used nowadays for example for monitoring the soot emissions of internal combustion engines and for on-board diagnosis (OBD), for example for functional monitoring of particle filters, for example of a diesel particle filter (DPF). In this case the exhaust gas is led along to the particle sensor downstream of the particle filter through a dual protective pipe construction. What is more, collecting resistive particle sensors are known that analyze a change in the electrical properties of an interdigital electrode structure that is due to particle deposits.

Two or more electrodes can be provided that preferably intermesh with each other in a comb-like manner and that are attached to a ceramic structure. The same are also referred to as interdigital electrodes (IDE) and form the actual sensor element. The electrodes are short-circuited by an increasing number of particles collecting on the particle sensor, which causes a decreasing electrical resistance with increasing particle collection, a decreasing impedance or a variation of a parameter related to the resistance or the impedance, such as a voltage and/or a current. In general, a threshold value, for example of a measurement current between the electrodes, is determined for analysis and the time to reach the threshold value is used as a measure of the collected amount of particles. Alternatively, a rate of change of a signal during the particle collection can be analyzed.

One such resistive particle sensor is described in DE 101 33 384 A1. The particle sensor is made up of two intermeshing comb-like electrodes that are at least partly covered by a capture sleeve. If particles from a gas flow collect on the particle sensor, then this results in an analyzable change in the impedance of the particle sensor, from which the amount of collected particles and hence the amount of particles carried along in the exhaust gas can be concluded.

If the particle sensor is fully loaded, the collected particles are combusted in a regeneration phase using a heating element that is integrated within the particle sensor. For this the ceramic of the sensor element is heated to high temperatures, usually of >600° C. In said regeneration phase the sensor element reacts sensitively to large local temperature changes or to a thermal shock, such as can occur as a result of incident water or drops of water. Such a thermal shock can result in cracks in the sensor element. Therefore, a sensor regeneration can only be requested by the engine controller if there can no longer be water at the sensor installation position according to a calculation of the amount of heat in the engine controller.

The document DE 10 2009 028 319 A1 discloses among other things a method for operating a particle sensor for determining a particle content in an exhaust gas flow of an internal combustion engine, wherein the particle sensor is subjected to a regeneration in regeneration phases at certain time intervals, and in doing so a soot load on the particle sensor is removed. The regeneration is carried out for this after waiting for a sensor release, wherein in the case of a cold start or in the case of a warm start of the internal combustion engine the particle sensor is subjected to drying with a heating element that is integrated therein. Said moisture protection heating is carried out with previously applied fixed times or by means of a drying model.

By strongly subjecting the exhaust system to water from the outside, for example when driving through water, or in the event of the penetration of water into the exhaust system, a marked cooling of the exhaust system can occur. Depending on the exhaust system configuration, said cooling may not be detected by the engine controller, but may result in a risk of thermal shock on the sensor element.

In order to dry the sensor element at the start of a driving cycle, a protective state is provided during the waiting period to a dew point end (DPE), in which the probe is heated to a low constant temperature. At said temperature the sensor element is indeed dried, but still no thermal shock can occur as a result of incident drops of liquid.

In order to ensure the regeneration of a dried sensor element at the starting point, the following conditions must be fulfilled:
- sensor operation in the "protective heating before the dew point end" phase for a certain minimum time, typically for example 80 s, and
- integration of the amount of heat necessary for the dew point end release in the engine controller.

With the previously used methods, there is however the possibility that driving through water during a sensor protective heating phase can result in wetting of the sensor element and the moisture no longer being able to be expelled from the sensor element until sensor regeneration is used. The aforementioned conditions would not provide adequate protection if the sensor element is subjected to liquid water while driving through water, for example shortly before the end of the "protective heating before the dew point end" phase. Neither the sensor nor the engine controller would detect said driving through water. Sometimes, a sensor regeneration could be carried out without complete drying out of the sensor element having occurred. Said sensor regeneration could result in damage to the sensor element.

A method for detecting at least one property of a fluid medium is known from DE 10 2010 002 979 A1, wherein a sensor element with at least one heating element and at least one temperature sensor is used, wherein in at least one droplet detection step of the method the sensor element is heated by means of the heating element. For this it is provided that the temperature of the sensor element is detected by means of the temperature sensor, wherein the impingement of a liquid from the fluid medium, in particular droplets, on the sensor element can be concluded from a brief drop in the temperature, in particular a temperature peak. In said document, however, no approach is described whereby the protective heating is adapted as a result of said droplet detection in order to guarantee a dried-out sensor element, for example after driving through water.

SUMMARY OF THE INVENTION

It is therefore the object of the invention that only a fully dried-out sensor element can be regenerated.

It is further the object of the invention to provide a suitable device for performing the method, in particular a control and analysis unit.

SUMMARY OF THE INVENTION

The object relating to the method is achieved by extending the duration of said heating phase before the regeneration phase during said heating phase, which is known as the "protective heating before the dew point end (DPE)", if a temperature deviation of a certain temperature bandwidth about a target temperature value is detected for a certain time. It can thus be achieved that the sensor element is always fully dried out, so that a sensor regeneration can be carried out at high temperatures without damage resulting from a thermal shock to the sensor element.

If, as a preferred version of the method provides, the duration of the temperature deviation and/or the temperature bandwidth (±ΔT) about the target temperature value, for example typically 200° C., can be predetermined, the sensitivity of the method can be adapted to the respective used components or to the arrangement of the components.

A preferred version of the method provides that a timer for controlling the duration of the heating phase prior to the regeneration phase is reset and/or restarted whenever a temperature deviation from the defined temperature bandwidth about the target temperature value is detected. Because of this, an adaptation of the duration of the heating phase can be enabled, depending on ambient conditions.

Regarding optimal planning of the regeneration phase, it can be provided that during each reset and/or restart of the timer, a counter is incremented and the count is analyzed to enable the regeneration phase. Because of this, for example defined minimum times to the start of the regeneration phase can be influenced.

A preferred version of the method provides that on reaching an applicable number of reset and/or restart processes, the sensor regeneration phase is blocked for a defined driving cycle. Thus in the event of strong cooling of the particle sensor, for example as a result of heavy wetting with water, damage to the particle sensor by a thermal shock when using the sensor regeneration phase with corresponding high temperatures can be avoided. In principle, a logic system that provides a minimum time in the "protective heating before DPE" state is already at least partly implemented in existing systems. The aspect of monitoring sensor wetting by water in the "protective heating before DPE" phase using related sensor cooling has not yet been considered.

One version of the method provides that heavy wetting with water of an exhaust system of an internal combustion engine, in particular of the particle sensor installed therein, is detected using the frequency of the reset and/or restart processes of the timer. Thus for example driving through water can be detected. In the course of protective measures, for example the regeneration of the sensor element can then be suspended until complete drying of the sensor element can be assumed. In addition, in the event of the detection of driving through water, suitable protective measures for other components of the emission control system can be initiated in order to prevent damage of the same.

A preferred application of the method and the versions thereof, such as have been described previously, provides the operation of a particle sensor in the context of on-board diagnosis of the particle sensor that is disposed in the exhaust system of an internal combustion engine, which is implemented as a diesel engine or as a gasoline engine, for on-board diagnosis of a particle filter or that is used for measuring raw soot emissions. In said application, in particular accurate and reproducible diagnosis of the particle load of the soot particle filter (DPF) disposed in the exhaust system of the diesel internal combustion engine takes place. For the protection of the particle sensor and other components of the emission control system of the internal combustion engine, the method according to the invention can provide advantages and assist in avoiding damage to the components of the emission control system, in particular in off-road vehicles in which strong cooling frequently occurs as a result of heavy wetting with water.

The object relating to the device is achieved in that the control and analysis unit comprises devices, such as at least one timer that can be re-initialized, at least one counter and one or a plurality of comparators for performing the method described above and the implemented method variants thereof. Said devices are usually already provided in control and analysis units according to the prior art. It is advantageous here that no hardware change has to be carried out on the particle sensor or on the control and analysis unit for performing the method. Said additional functionality can be achieved exclusively with a software enhancement. The control and analysis unit can be implemented in this case as an independent unit, which can be implemented for example close to the particle sensor or as an integral component of an overarching engine controller.

BRIEF DESCRIPTION OF THE DRAWINGS

The invention is described in detail below using an exemplary embodiment that is illustrated in the figures. In the figures.

DETAILED DESCRIPTION

Figure 1:
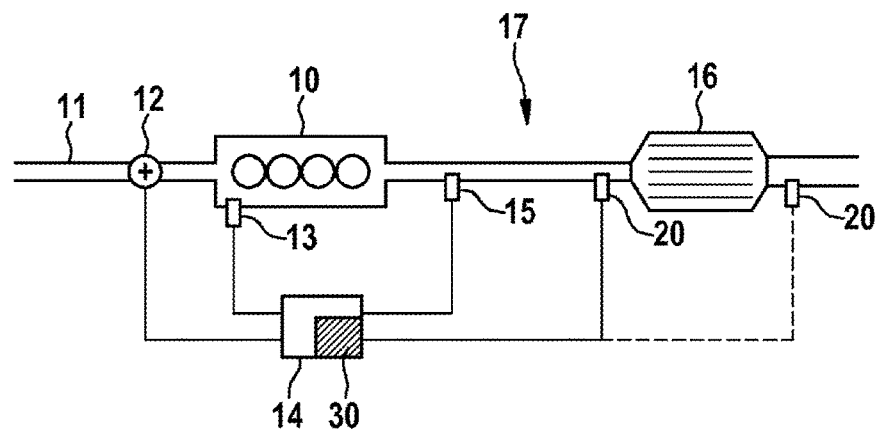
FIG. 1 shows in a schematic representation the technical environment in which the method can be used and FIG. 2 shows schematically a particle sensor in an exploded representation.

FIG. 1 shows schematically the technical environment in which the method according to the invention can be used. An internal combustion engine 10, which can be implemented as a diesel engine, receives combustion air that is delivered by means of an air feed 11. During this the amount of the combustion air can be determined by means of an air mass flowmeter 12 in the air feed 11. The amount of air can be used during the correction of a probability of deposition of particles present in the exhaust gas of the internal combustion engine 10. The exhaust gas of the internal combustion engine 10 is discharged by means of an exhaust system 17 in which an emission control system 16 is disposed. Said emission control system 16 can be implemented as a diesel particle filter. Furthermore, an exhaust gas probe that is implemented as a lambda probe 15 and a particle sensor 20 are disposed in the exhaust system 17, the signals of which are fed to an engine controller 14 or a special control and analysis unit 30 (Sensor Control Unit SCU), which can be implemented as a component of the engine controller 14 or as an independent unit, for example close to the particle sensor 20. The engine controller 14 is also connected to the air mass flowmeter 12 and determines, based on the data delivered to it, an amount of fuel that can be fed to the internal combustion engine 10 by means of a fuel metering means 13.

In this case the particle sensor 20 can also be disposed after the emission control system 16 in the direction of flow of the exhaust gas, which brings with it advantages in respect of the homogenization of the flow of exhaust gas at this point and in particular when used during the on-board diagnosis. With the devices shown, observation of the particle emissions of the internal combustion engine 10 and a prognosis of the load on the emission control system 16 in the form of a diesel particle filter (DPF) are possible.

Figure 2:
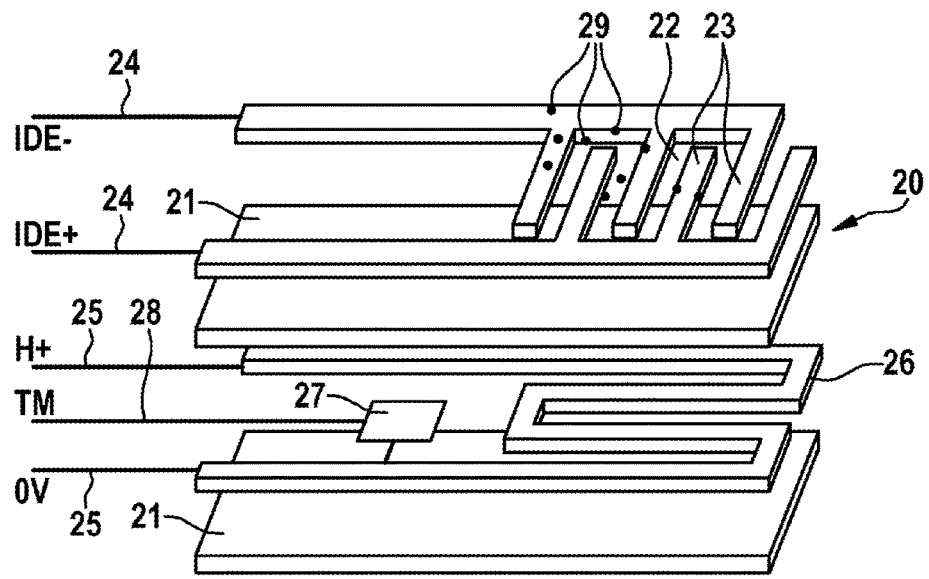

FIG. 2 shows in a schematic representation a particle sensor 20 corresponding to the prior art in an exploded representation.

An IDE measurement structure 22 in the form of a first electrode and a second electrode is mounted on insulating support layers 21 of ceramic, for example of aluminum oxide. The electrodes are implemented in the form of two interdigital, intermeshed comb electrodes and are referred to as IDE electrodes 23 and constitute the actual sensor element. The IDE connections 24 (IDE+ and IDE−), by means of which the IDE electrodes 23 are connected to the control and analysis unit 30 (not shown in FIG. 2) for supplying voltage and for performing the measurement, are provided on the end faces of the IDE electrodes 23. In addition, in the example shown a heating element 26, which is connected to the control and analysis unit 30 by means of additional heating element connections 25 (H+, 0V), is integrated between the insulating support layers 21.

In addition, a temperature sensor 27 can be provided in the layer structure of the particle sensor 20 for measuring the temperature, wherein a temperature sensor connection 28 (TM) is also led out of the particle sensor 20. For example, resistance structures of platinum can be used as a temperature sensor 27. Alternatively, at least a part of the structure of the heating element 26 can also be used as a temperature sensor 27.

If such a particle sensor 20 is operated in a gas flow carrying soot particles 29, for example in an exhaust duct of a diesel engine or a furnace, then soot particles 29 from the gas flow are deposited on the particle sensor 20. Said particles have a certain electrical conductivity. During this the rate of deposition of the soot particles 29 on the particle sensor 20 depends, besides on the particle concentration in the exhaust gas, among other things also on the voltage that is applied to the IDE electrodes 23. An electrical field is produced by the applied voltage and exerts a corresponding attraction on electrically charged soot particles 29. Therefore, the rate of deposition of the soot particles 29 can be influenced by the suitable selection of the voltage applied to the IDE electrodes 23.

In the exemplary embodiment, the IDE electrodes 23 and the top insulating support layer 21, on which the IDE electrodes 23 are disposed, are covered by means of a protective layer (shown in dashed form). Said optional protective layer protects the IDE electrodes 23 against corrosion at the generally prevailing high operating temperatures of the particle sensor 20. In the present exemplary embodiment, it is made of a material with a low conductivity, but can also be made of an insulator.

Soot particles 29 from the gas flow have been deposited in the form of a layer on the protective layer. Owing to the low conductivity protective layer, the soot particles 29 form a conductive path between the IDE electrodes 23, so that, depending on the amount of deposited soot particles 29, a change of resistance between the IDE electrodes 23 results. This can for example be measured by applying a constant voltage to the IDE connections 24 of the IDE electrodes 23 and determining the change of the current that is due to the collected soot particles 29. If the protective layer is made insulating, the deposited soot particles 29 result in a change of the impedance of the particle sensor 20, which can be analyzed by means of a suitable measurement, preferably with an alternating voltage.

If the particle sensor 20 is loaded so much with a layer of soot particles 29 that additional deposited soot particles 29 do not result in an additional change of the resistance or the impedance of the particle sensor 20, then the particle sensor 20 is regenerated within a regeneration phase. At the same time the particle sensor 20 is heated up using the heating element 26 to the extent that the deposited soot particles 29 are combusted. This usually happens at temperatures >600° C.

Before regeneration of the particle sensor 20, protective heating is carried out for a certain time before the dew point end (DPE), as initially described. According to the invention, it is provided in this case that a timer for the time in the "protective heating before the dew point end" phase is reset if the sensor temperature leaves a predefinable temperature window for an applicable time during the protective heating.

Typically, the predefinable temperature window is 200° C.±15 K. A time duration for the "protective heating before the dew point end" phase can typically be 80 s for this, with which the timer is initialized at the start of said phase. Wetting the sensor element with water in the "protective heating before the dew point end" phase results in a larger temperature deviation, because the heating regulator for the heating element 26 is only operated with an applicable maximum heating power and thus cannot evaporate the water fast enough.

As long as the sensor element is in the temperature range of for example 200° C.±ΔT K, the timer is decremented every second until the "protective heating before the dew point end" phase is ended, and then the sensor regeneration phase can be started. The parameter ΔT can be predefined for this. It is assumed that no heavy wetting and cooling connected therewith have taken place and the particle sensor 20 can be safely regenerated at suitable high temperatures following said protective heating.

Once the sensor element leaves the predefinable temperature window for an applicable time duration as a result of strong cooling, the timer is reset again and re-initialized with the predefinable time duration for the "protective heating before the dew point end" phase, in this case for example 80 s, wherein each re-initialization of the timer results in an incrementation of a "re-initialization of protective heating timer" counter. On reaching a likewise applicable number of re-initializations of the counter, a sensor regeneration in this driving cycle is blocked because it is assumed therefrom that the sensor is not yet sufficiently dried out as a result of frequent and/or heavy water contact during said phase.

The functionality described above is preferably implemented as a software module in a local controller of the particle sensor 20, i.e. in a control and analysis unit 30 of the particle sensor 20. However, this can also be an integral component of the overarching engine controller 14 (cf. FIG. 1).

Thus it can be achieved that the sensor element is always fully dried out, so that a regeneration can be carried out at high temperatures without damage as a result of a thermal shock to the sensor element.

The invention claimed is:

1. A method for operating a particle sensor (20) for determining a particle content in a gas flow, wherein the particle sensor (20) comprises on a surface thereof a sensor structure for determining a soot load and at least one heating element (26) that is separated by an insulating layer from the sensor structure, the heating element being configured to heat up the particle sensor (20) in a regeneration phase to remove a soot load on the particle sensor (20), and the heating element being configured to carry out a heating phase at least at times before the regeneration phase, wherein a significantly lower temperature is controlled in said heating phase compared to a temperature of the regeneration phase, wherein a temperature sensor (27) is configured to detect brief drops in temperature as a result of wetting by water, the temperature sensor (27) being integrated within the particle sensor (20), the method comprising, during said heating phase before the regeneration phase, extending the duration of said heating phase whenever a temperature deviation from a defined temperature bandwidth about a target temperature value is detected for a certain time, wherein a timer is provided for control of the duration of the heating phase before the regeneration phase, wherein the timer is reset and/or restarted whenever a temperature deviation from the defined temperature bandwidth about the target temperature value is detected.

2. The method as claimed in claim 1, characterized in that the temperature bandwidth about the target temperature value is predefined.

3. The method as claimed in claim 1, characterized in that during each resetting and/or restarting of the timer, a counter is incremented and the count is analyzed to enable the regeneration phase.

4. The method as claimed in claim 3, characterized in that, on reaching an applicable number of reset and/or restart processes, the regeneration phase is blocked for a defined driving cycle.

5. The method as claimed in claim 3, characterized in that using a frequency of the reset and/or restart processes of the timer, heavy wetting by water of an exhaust system (17) of an internal combustion engine (10) is detected.

6. The method as claimed in claim 1, wherein the particle sensor (20) is disposed in an exhaust system (17) of an internal combustion engine (1), further comprising performing an on-board diagnosis of a particle filter.

7. The method as claimed in claim 6, wherein the internal combustion engine is a diesel engine.

8. The method as claimed in claim 6, wherein the internal combustion engine is a gasoline engine.

9. A method for operating a particle sensor (20) for determining a particle content in a gas flow, wherein the particle sensor (20) comprises on a surface thereof a sensor structure for determining a soot load and at least one heating element (26) that is separated by an insulating layer from the sensor structure, the heating element being configured to heat up the particle sensor (20) in a regeneration phase to remove a soot load on the particle sensor (20), and the heating element being configured to carry out a heating phase at least at times before the regeneration phase, wherein a significantly lower temperature is controlled in said heating phase compared to a temperature of the regeneration phase, wherein a temperature sensor (27) is configured to detect brief drops in temperature as a result of wetting by water, the temperature sensor (27) being integrated within the particle sensor (20), the method comprising, during said heating phase before the regeneration phase, extending the duration of said heating phase when a temperature deviation from a defined temperature bandwidth about a target temperature value is detected for a certain time, characterized in that using a frequency of reset and/or restart processes of a timer, heavy wetting by water of an exhaust system (17) of the particle sensor installed in an internal combustion engine (10) is detected.

10. A method for operating a particle sensor (20) for determining a particle content in a gas flow, wherein the particle sensor (20) comprises on a surface thereof a sensor structure for determining a soot load and at least one heating element (26) that is separated by an insulating layer from the sensor structure, the heating element being configured to heat up the particle sensor (20) in a regeneration phase to remove a soot load on the particle sensor (20), and the heating element being configured to carry out a heating phase at least at times before the regeneration phase, wherein a significantly lower temperature is controlled in said heating phase compared to a temperature of the regeneration phase, wherein a temperature sensor (27) is configured to detect brief drops in temperature as a result of wetting by water, the temperature sensor (27) being integrated within the particle sensor (20), the method comprising, during said heating phase before the regeneration phase, extending the duration of said heating phase if a temperature deviation from a defined temperature bandwidth about a target temperature value is detected for a certain time, characterized in that a timer for control of the duration of the heating phase before the regeneration phase is reset and/or restarted whenever a temperature deviation from the defined temperature bandwidth about the target temperature value is detected.

* * * * *